United States Patent [19]

Wächtler et al.

[11] Patent Number: 4,871,470

[45] Date of Patent: Oct. 3, 1989

[54] CYCLOHEXANE DERIVATIVES

[75] Inventors: Andreas Wächtler, Griesheim; Joachim Krause, Dieburg; Rudolf Eidenschink, Mühltal; Georg Weber, Erzhausen, all of Fed. Rep. of Germany

[73] Assignee: Merck Patent Gesellschaft mit Beschrankter Haftung, Darmstadt, Fed. Rep. of Germany

[21] Appl. No.: 130,358

[22] PCT Filed: Feb. 17, 1987

[86] PCT No.: PCT/EP87/00090

§ 371 Date: Oct. 30, 1987

§ 102(e) Date: Oct. 30, 1987

[87] PCT Pub. No.: WO87/05293

PCT Pub. Date: Sep. 11, 1987

[30] Foreign Application Priority Data

Mar. 1, 1986 [DE] Fed. Rep. of Germany ....... 3606788
Nov. 4, 1986 [DE] Fed. Rep. of Germany ....... 3637442

[51] Int. Cl.[4] .................. C09K 19/30; C07C 13/28; C07C 69/753; C07C 121/46; C07C 49/313; C07C 43/21; C07C 39/17

[52] U.S. Cl. .................. 252/299.63; 350/350 R; 350/350 S; 558/414; 558/415; 558/416; 558/423; 558/425; 558/426; 558/431; 560/59; 560/60; 560/62; 560/55; 560/8; 560/102; 560/116; 560/129; 560/188; 560/255; 568/329; 568/367; 568/631; 568/642; 568/659; 568/661; 568/664; 568/816; 568/743; 568/744; 568/745; 568/746; 568/747; 570/129; 570/130; 570/182; 570/188; 585/20; 585/25

[58] Field of Search .......... 252/299.63; 350/350 R, 350/350 S; 585/20, 25; 570/129, 130, 182, 188; 558/414, 415, 416, 423, 425, 426, 431; 560/59, 60, 62, 55, 102, 8, 116, 188, 255, 129; 568/329, 367, 642, 631, 659, 661, 664, 816, 743, 744, 746, 745, 747

[56] References Cited

U.S. PATENT DOCUMENTS

| | | | |
|---|---|---|---|
| 4,419,263 | 12/1983 | Praefcke et al. | 252/299.63 |
| 4,431,853 | 2/1984 | Sato et al. | 252/299.63 |
| 4,514,044 | 4/1985 | Gunjima et al. | 252/299.63 |
| 4,558,151 | 12/1985 | Takatsu et al. | 252/299.63 |
| 4,583,826 | 4/1986 | Petrzilka et al. | 252/299.63 |
| 4,610,805 | 9/1986 | Schellenberger et al. | 252/299.63 |
| 4,630,896 | 12/1986 | Petrzilka et al. | 252/299.63 |
| 4,637,897 | 1/1987 | Kelly et al. | 252/299.63 |
| 4,659,502 | 4/1987 | Fearon et al. | 252/299.63 |
| 4,695,131 | 9/1987 | Balkwill et al. | 252/299.63 |
| 4,724,097 | 2/1988 | Romer et al. | 252/299.63 |

FOREIGN PATENT DOCUMENTS

| | | | |
|---|---|---|---|
| 84194 | 7/1983 | European Pat. Off. | 252/299.63 |
| 3226051 | 2/1983 | Fed. Rep. of Germany | 252/299.63 |
| 59-110631 | 6/1984 | Japan | 252/299.63 |

Primary Examiner—Teddy S. Gron
Attorney, Agent, or Firm—Millen, White & Zelano

[57] ABSTRACT

Cyclohexane derivatives of formula I

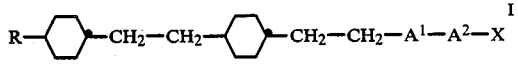

wherein
R is an alkyl group which has 1-12 C atoms and in which one or two non-adjacent CH$_2$ groups can also be replaced by O, —CO—O— or —OCO—,
A$^1$ and A$^2$ each independently of one another are trans-1,4-cyclohexylene or unsubstituted or fluorine-substituted 1,4-phenylene, and one of the groups A$^1$ and A$^2$ can also be a single bond,
X is —CN, halogen, OH, —COOR$^1$, —OOCR$^1$, —COR$^1$, —OR$^1$ or R$^1$ and
R$^1$ is an alkyl group which has 1-12 C atoms and in which one or two CH$_2$ groups can also be replaced by O, but excluding direct links between two O atoms,
with the proviso that, in the case of X=CN, A$^2$ is trans-1,4-cyclohexylene or fluorine-substituted, 1,4-phenylene, are suitable as components of liquid-crystalline phases.

10 Claims, No Drawings

CYCLOHEXANE DERIVATIVES

The invention relates to novel cyclohexane derivatives of the formula I

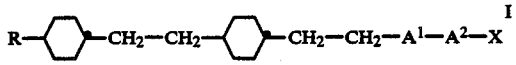
    I in which

R is an alkyl group which has 1-12 C atoms and in which one or two non-adjacent CH$_2$ groups can also be replaced by O, —CO—O— or —OCO—, A$^1$ and A$^2$ each independently of one another are trans-1,4-cyclohexylene or unsubstituted or fluorine-substituted 1,4-phenylene, and one of the groups A$^1$ and A$^2$ can also be a single bond, X is —CN, halogen, OH, —COOR$^1$, —OOCR$^1$, —COR$^1$, —OR$^1$ or R$^1$ and R$^1$ is an alkyl group which has 1-12 C atoms and in which one or two CH$_2$ groups can also be replaced by O, but excluding direct links between two O atoms, with the proviso that, in the case of X=CN, A$_2$ is trans-1,4-cyclohexylene or fluorine-substituted 1,4-phenylene.

The compounds of the formula I can, like similar compounds, for example those known from German Offenlegungsschrift No. 2,702,598, be used as components of liquid-crystalline dielectrics, especially for displays based on the principle of the twisted cell, the guest/host effect, the effect of the deformation of aligned phases or the effect of dynamic scattering.

It was the object of the invention to discover novel stable liquid-crystalline or mesogenic compounds which are suitable as components of liquid-crystalline dielectrics.

It has been found that the compounds of the formula I are outstandingly suitable as components of liquid-crystalline dielectrics Especially, using these components, stable liquid-crystalline phases of a relatively low optical anisotropy and of a high nematic character can be prepared, which, in electro-optical display elements according to the principle of the twisted cell and/or the guest/host effect, are distinguished by a particularly advantageous angular dependence of the contrast.

Moreover, by providing the compounds of the formula I, the range of liquid-crystalline substances which are suitable under various application aspects for the preparation of nematic mixtures is in general considerably extended.

The compounds of the formula I have a wide range of applications. Depending on the selection of the substituents, these compounds can be used as base materials of which the predominant part of liquid-crystalline phases is composed, but compounds of the formula I can also be added to liquid-crystalline base materials from other classes of compounds, for example in order to influence the angular dependence of the contrast and/or the optical anisotropy of such a phase. The compounds of the formula I are also suitable as intermediates for the preparation of other substances which can be used as constituents of liquid-crystalline dielectrics.

In the pure state, the compounds of the formula I are colorless and form liquid-crystalline mesophases within a temperature range which is advantageous for electro-optical use. They are very stable chemically, thermally and towards light.

The invention thus relates to compounds of the formula I and to a process for their preparation, which is characterized in that, for preparing carbonitriles of the formula I (X=CN), the corresponding carboxylic acids (X=COOH) or one of their reactive derivatives are converted to the corresponding acid amides and the latter are dehydrated, or a corresponding acid chloride is reacted with sulfamide, or that, for preparing carboxylic acid esters of the formula I (X=—COOR$^1$), the corresponding carboxylic acid compounds or one of their reactive derivatives are reacted with the corresponding alcohol or one of its reactive derivatives, or that, for preparing acyl compounds of the formula I (X=—COR$^1$), the corresponding carboxylic acid compounds or one of their reactive derivatives are converted to the corresponding nitriles and the latter are reacted with the corresponding Grignard compound, or that, for preparing the alkyl compounds (X=R$^1$), the corresponding carboxylic acid compounds or one of their reactive derivatives are converted to the corresponding keto compounds (X=—COR$^1$) and the latter are reduced, or that a compound which otherwise corresponds to the formula I but contains one or more reducible groups and/or C—C bonds in place of H atoms is treated with a reducing agent, or that, for preparing alkoxy compounds (X=—OR$^1$), the corresponding alcohols (R$^1$=OH) or one of their reactive derivatives are etherified, or that, for preparing alkanoyloxy derivatives of the formula I (X=—OOCR$^1$) the corresponding alcohols (X=OH) or one of their reactive derivatives are reacted with a corresponding carboxylic acid or one of its reactive derivatives.

The invention also relates to the use of the compounds of the formula I as components of liquid-crystalline phases. Furthermore, the invention relates to liquid-crystalline phases containing at least one compound of the formula I, and to liquid crystal display elements, in particular electro-optical display elements, which contain such phases.

For the sake of simplicity, "Cyc" below is a 1,4-cyclohexylene group, Phe is a 1,4-phenylene group and PhF is a fluorine-substituted 1,4-phenylene group.

In the compound of the formula I, those stereoisomers are preferred in which all the 1,4-cyclohexylene groups are trans-substituted in the 1,4-positions.

Accordingly, the compounds of the formula I comprise preferred compounds of the part formulae Ia to Iab

    Ia

    Ib

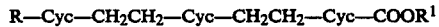    Ic

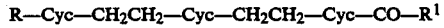    Id $$R-Cyc-CH_2CH_2-Cyc-CH_2CH_2-Cyc-OOCR^1 \quad \text{Ie}$$

$$R-Cyc-CH_2CH_2-Cyc-CH_2CH_2-Cyc-CH_2OAlkyl \quad \text{If}$$

$$R-Cyc-CH_2CH_2-Cyc-CH_2CH_2-Cyc-OR^1 \quad \text{Ig}$$

$$R-Cyc-CH_2CH_2-Cyc-CH_2CH_2-Phe-R^1 \quad \text{Ih}$$

$$R-Cyc-CH_2CH_2-Cyc-CH_2CH_2-Phe-OR^1 \quad \text{Ii}$$

$$R-Cyc-CH_2CH_2-Cyc-CH_2CH_2-Phe-Halogen \quad \text{Ij}$$

$$R-Cyc-CH_2CH_2-Cyc-CH_2CH_2-Phe-OOCR^1 \quad \text{Ik}$$

$$R-Cyc-CH_2CH_2-Cyc-CH_2CH_2-PhF-CN \quad \text{Il}$$

$$R-Cyc-CH_2CH_2-Cyc-CH_2CH_2-PhF-Halogen \quad \text{Im}$$

$$R-Cyc-CH_2CH_2-Cyc-CH_2CH_2-Cyc-Cyc-R^1 \quad \text{In}$$

$$R-Cyc-CH_2CH_2-Cyc-CH_2CH_2-Cyc-Phe-R^1 \quad \text{Io}$$

$$R-Cyc-CH_2CH_2-Cyc-CH_2CH_2-Cyc-Phe-OR^1 \quad \text{Ip}$$

$$R-Cyc-CH_2CH_2-Cyc-CH_2CH_2-Cyc-PhF-Halogen \quad \text{Iq}$$

$$R-Cyc-CH_2CH_2-Cyc-CH_2CH_2-Cyc-PhF-CN \quad \text{Ir}$$

$$R-Cyc-CH_2CH_2-Cyc-CH_2CH_2-Phe-Phe-R^1 \quad \text{Is}$$

$$R-Cyc-CH_2CH_2-Cyc-CH_2CH_2-Phe-Phe-OR^1 \quad \text{It}$$

$$R-Cyc-CH_2CH_2-Cyc-CH_2CH_2-PhF-Phe-R^1 \quad \text{Iu}$$

$$R-Cyc-CH_2CH_2-Cyc-CH_2CH_2-PhF-Phe-OR^1 \quad \text{Iv}$$

$$R-Cyc-CH_2CH_2-Cyc-CH_2CH_2-Phe-PhF-R^1 \quad \text{Iw}$$

$$R-Cyc-CH_2CH_2-Cyc-CH_2CH_2-Phe-PhF-OR^1 \quad \text{Ix}$$

$$R-Cyc-CH_2CH_2-Cyc-CH_2CH_2-Phe-PhF-Halogen \quad \text{Iy}$$

$$R-Cyc-CH_2CH_2-Cyc-CH_2CH_2-Phe-PhF-CN \quad \text{Iz}$$

$$R-Cyc-CH_2CH_2-Cyc-CH_2CH_2-Phe-Cyc-R^1 \quad \text{Iaa}$$

$$R-Cyc-CH_2CH_2-Cyc-CH_2CH_2-PhF-Cyc-R^1 \quad \text{Iab}$$

Preferably, compounds of the part formulae Ia–Ic and Ie, especially Ia, Ib and Ie, are used. It, and Ic are particularly preferred. Compounds of the part formulae Ih, Ii, Ij, Il, Im, Io, Iy and Iaa, especially Ih, Il and Im, are also preferred. Ih is particularly preferred.

Halogen is preferably chlorine or fluorine, and particularly preferably fluorine.

In the group PhF the fluorine atom is preferably in the ortho-position to X.

If X is halogen, $A^2$ is preferably Phe or PhF.

$A^1$–$A^2$ is preferably Cyc, Phe, Phe-Cyc, Phe-Phe, PhF-Phe or Phe-PhF, particularly preferably Cyc or Phe.

X is preferably $R^1$, $OR^1$, CN or halogen, and particularly preferably $R^1$ or halogen.

$R^1$ is preferably an alkyl group having preferably 2 to 7 C atoms.

In the compounds of the formulae above and below, the alkyl radicals R, in which one $CH_2$ group can be replaced by a O atom ("alkoxy" or "oxaalkyl") or two nonadjacent $CH_2$ groups can be replaced by O atoms ("alkoxy-alkoxy" or "dioxaalkyl"), can be straight-chain or branched. Preferably, they are straight-chain, have 2, 3, 4, 5, 6, 7, 8, 9 or 10 C atoms and accordingly are preferably ethyl, propyl, butyl, pentyl, hexyl, heptyl, octyl, nonyl, decyl, ethoxy, propoxy, butoxy, pentoxy, hexoxy, heptoxy, octoxy, nonoxy, decoxy, 2-oxapropyl (=methoxy methyl), 2-(=ethoxymethyl) or 3-oxabutyl (=2- methoxy methyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, and also methyl, undecyl, dodecyl, methoxy, undecoxy, dodecoxy, 2-, 3-, 4-, 5-, 6-, 7-, 8-, 9- or 10-oxaundecyl, 2-, 3-, 4-, 5-, 6-, 7-, 8-, 9-, 10- or 11-oxadodecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6- or 4,6-dioxaheptyl, 1,3-, 1,4-, 1,5-, 1,6-, 1,7-, 2,4-, 2,5-, 2,6-, 2,7-, 3,5-, 3,6-, 3,7-, 4,6-, 4,7- or 5,7-dioxaoctyl, 1,3-, 1,4-, 1,5-, 1,6-, 1,7-, 1,8-, 2,4-, 2,5-, 2,6-, 2,7-, 2,8-, 3,5-, 3,6-, 3,7-, 3,8-, 4,6-, 4,7-, 4,8-, 5,7- or 5,8-dioxanonyl, 1,3-, 1,4-, 1,5-, 1,6-, 1,7-, 1,8-, 1,9-, 2,4-, 2,5-, 2,6-, 2,7-, 2,8-, 2,9-, 3,5-, 3,6-, 3,7-, 3,8-, 3,9-, 4,6-, 4,7-, 4,8-, 4,9-, 5,7-, 5,8- or 5,9-dioxadecyl.

R is preferably alkyl or alkoxy, in particular n-alkyl.

Compounds of the formulae I and Ia to Ig with branched wing groups R or $R^1$ may sometimes be of importance because of higher solubility in the usual liquid-crystalline base materials, and in particular as chiral doping substances if they are optically active. Branched groups of this type contain as a rule no more than one chain branch. Preferred branched radicals R and $R^1$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl and 3-oxa-4-methylpentyl. Compounds of this type are suitable as components of ferro-electric liquid crystal phases.

Amongst the compounds of the formulae I and Ia to Ig, those are preferred in which at least one of the radicals contained therein has one of the indicated preferred meanings.

The compounds of the formula I can be prepared by methods known per se, such as are described in the literature (for example in the standard books like Houben-Weyl, Methoden der Organischen Chemie [Methods of organic chemistry], Georg-Thieme-Verlag, Stuttgart), namely under reaction conditions which are known and suitable for the reactions listed. Variants which are known per se and not mentioned here in more detail can also be used here.

If desired, the starting materials can also be formed in situ, in such a way that they are not isolated from the reaction mixture but immediately reacted further to give the compounds of the formula I. The starting materials used are preferably the known p-[trans-4-(trans-4-R-cyclohexylethyl)-cyclohexylethyl]-benzonitriles, or the carboxylic acids obtainable by hydrolysis of the latter. Apart from the corresponding free carboxylic acids, their reactive derivatives are also suitable. Especially the acid halides, above all the chlorides and bromides, and also the anhydrides, azides or esters, in particular alkyl esters having 1-4 C atoms in the alkyl group, are suitable reactive derivatives of the said carboxylic acids.

The reactive derivatives of the said alcohols can especially be the corresponding metal alcoholates, wherein M is an equivalent of a metal, preferably of an alkaline metal such as Na or K.

For preparing the nitriles of the formula I (X=CN), corresponding acid amides in which a $CONH_2$ group takes the place of the CN groups, can be dehydrated. The amides are obtainable, for example, from the corresponding acid halides by reaction with ammonia. The corresponding acid halides can in turn be prepared in a known manner from the corresponding carboxylic acids, for example by means of thionyl chloride. Examples of suitable dehydrating agents for the dehydration of the amides are inorganic acid chlorides such as $SOCL_2$, $PCL_3$, $PCL_5$, $POCL_3$, $SO_2CL_2$ and $COCL_2$, and also $P_2O_5$, $AlCL_3$ (for example as a double compound with NaCl), aromatic sulfonic acids and sulfonic acid halides. These can be used in the presence or absence of an inert solvent at temperatures between about 0° and 150° C.; examples of possible solvents are bases such as pyridine of triethylamine, aromatic hydrocarbons such as benzene, toluene or xylene, or amides such as DMF.

For preparing the nitriles of the formula I, corresponding acid halides preferably the chlorides, can also be reacted with sulfamide, advantageously in an inert solvent such as tetramethylene sulfone at temperatures between about 80° and 150°, preferably at 120°. After conventional work-up, the nitriles can be isolated directly.

For preparing the esters of the formula I (X=—$OOCR^1$), preferably a corresponding alcohol or one of its reactive derivatives is reacted with a corresponding carboxylic acid or one of its reactive derivatives.

Reactive derivatives of the said alcohols are in particular the corresponding metal alcoholates of the formula $R^1OM$, wherein M is an equivalent of a metal, preferably an alkali metal such as Na or K.

Suitable reactive derivatives of the said carboxylic acids are especially the acid halides, above all the chlorides and bromides, and also the anhydrides, azides or esters, in particular alkyl esters having 1-4 C atoms in the alkyl group.

The esterification is advantageously carried out in the presence of an inert solvent. Especially ethers such as diethyl ether, di-n-butyl ether, THF, dioxane or anisole, ketones such as acetone, butanone or cyclohexanone, amides such as DMF or phosphoric acid hexamethyltriamide, hydrocarbons such as benzene, toluene or xylene, halogenohydrocarbons such as carbon tetrachloride or tetrachloroethylene, and sulfoxides such as dimethyl sulfoxide or sulfolane, are very suitable. Water-immiscible solvents can at the same time be used advantageously for azeotropically distilling off the water formed in the esterification. Occasionally, it is also possible to use an excess of an organic base, for example pyridine, quinoline or triethylamine, as the solvent for the esterification. The esterification can also be carried out in the absence of a solvent, for example by simple heating of the components in the presence of sodium acetate. The reagent temperature is usually between −50° and +250°, preferably between −20° and +80°. At these temperatures, the esterification reactions are as a rule complete after 15 minutes to 48 hours.

In detail, the reaction conditions for the esterification depend largely on the nature of the starting materials used. Thus, a free carboxylic acid is reacted with a free alcohol as a rule in the presence of a strong acid, for example a mineral acid such as hydrochloric acid or sulfuric acid. A preferred reaction procedure is the reaction of an acid anhydride or especially an acid chloride with an alcohol, preferably in a basic medium, important bases being especially alkali metal carbonates or bicarbonates such as sodium carbonate, sodium bicarbonate, potassium carbonate or potassium bicarbonate, alkali metal acetates such as sodium acetate or potassium acetate, alkaline earth metal hydroxides such as calcium hydroxide, or organic bases such as triethylamine, pyridine, lutidine, collidine or quinoline. In a further preferred esterification method, the alcohol is first converted to the sodium or potassium alcoholate, for example by treatment with ethanolic sodium or potassium hydroxide solution, the alcoholate is isolated and, together with sodium bicarbonate or potassium carbonate, suspended with stirring in acetone or diethyl ether, and a solution of the acid chloride or anhydride in diethyl ether, acetone or DMF is added to this suspension, advantageously at temperatures between about −25° and +20°.

For preparing the acyl compounds of the formula I (X=—CO—$R^1$) from the corresponding carboxylic acids, the corresponding nitrile is first prepared as described. The latter is reacted in a manner known per se with preferably a Grignard compound of the general formula R¹MHal, wherein M is a metal, preferably magnesium, and Hal is a halogen, preferably bromide, and the product is then hydrolysed. The Grignard compound is prepared in a known manner with magnesium and the corresponding alkyl halide R¹Hal, preferably R¹Br, in ether, preferably diethyl ether or tetrahydrofuran, under the conditions usual for such reactions.

For preparing alkyl compounds of the formula I (X=R¹), preferably the corresponding ketones (X=—CO—R¹) are reduced by the Clemmensen method (with zinc, amalgamated zinc or tin and hydrochloric acid, advantageously in an aqueous-alcoholic solution or in a heterogeneous phase with water/toluene at temperatures between about 80° and 120°) or by the Wolff-Kishner method (with hydrazine, advantageously in the presence of alkali such as KOH or NaOH in a high-boiling solvent such as diethylene glycol or triethylene glycol at temperatures between about 100° and 200°) to give the corresponding compounds of the formula I.

The compounds of the formula I can also be prepared by reducing compounds which otherwise correspond to the formula I but which contain one or more reducible groups and/or C—C bonds in place of H atoms.

Possible reducible groups are preferably carbonyl groups, in particular keto groups, and also, for example, free or esterified hydroxyl groups Preferred starting materials for the reduction correspond to the formula I, but they can contain a cyclohexene ring or cyclohexanone ring in place of a cyclohexane ring and/or a —CO— group in place of a —CH₂CH₂— group and/or a —CO— group in place of a —CH₂— group and/or a free or functionally modified (for example in the form of a p-toluenesulfonate) OH group in place of an H atom.

The reduction can be carried out, for example, by catalytic hydrogenation at temperatures between about 0° and about 200° and under pressures between about 1 and 200 bar in an inert solvent, for example an alcohol such as methanol, ethanol or isopropanol, an ether such as tetrahydrofuran (THF) or dioxane, an ester such as ethyl acetate, a carboxylic acid such as acetic acid, or a hydrocarbon such as cyclohexane. Advantageous suitable catalysts are rare metals such as Pt or Pd, which can be employed in the form of oxides (for example PtO₂, PdO), on a support (for example Pd on carbon, calcium carbonate or strontium carbonate) or in a finely dispersed form.

For preparing aromatic compounds of the formula I (wherein A¹-A² contains at least one unsubstituted or substituted 1,4-phenylene group), preferably trans-4-(trans-4-R-cyclohexylethyl)-cyclohexylacetonitriles are reacted with metal organic compounds, preferably with Grignard compounds of the BrMg-A¹-A²-X type or corresponding lithium compounds. The resulting ketones are reduced by catalytic hydrogenation according to processes known from the literature (for example Houben-Weyl 7/2a, pages 603 et seq.), either directly or after verification, to the corresponding alcohols, from which H₂O is then eliminated.

To prepare the ethers of the formula I, preferably a corresponding alcohol or one of its reactive derivatives is reacted with a corresponding alkyl halide, alkyl sulfonate or dialkyl sulfate, preferably in an inert solvent such as acetone, 1,2-dimethoxyethane, DMF or dimethyl sulfoxide, or in an excess of aqueous or aqueous-alcoholic NOAH or KOH at temperatures between about 20° and 100°.

Preferably, the hydroxy compound is first converted a corresponding metal derivative, for example by treatment with NaH, NaNH₂, NaOH, KOH, Na₂CO₃ or K₂CO₃ to the corresponding alkali metal alcoholate.

The dielectrics according to the invention consist of 2 to 25 and preferably 3 to 15 components, which include at least one compound of the formula I. The other constituents are preferably selected from the nematic or nematogenic substances, in particular the known substances, from the classes of azoxybenzenes, benzylideneanilines, biphenyls, terphenyls, phenyl or cyclohexyl benzoates, phenyl or cyclohexyl cyclohexanecarboxylates, phenyl cyclohexanes, cyclohexylbiphenyls, cyclohexylcyclohexanes, cyclohexylnaphthalenes, 1,4-bis-cyclohexylbenzenes, 4,4-bis-cyclohexylbiphenyls, phenyl- or cyclohexyl-pyrimidines, phenylor cyclohexyl-dioxanes, 1,2-bis-cyclohexylethanes, 1-cyclohexyl 2-phenylethanes, 1,2-bis-phenylethanes, stilbenes which cinnamic acids.

The most important compounds which can be used as constituents of such liquid-crystalline dielectrics can be characterized by the formula II:

in which L and E are each a carbocyclic or heterocyclic ring system selected from a group comprising 1,4-phenylene and trans-1,4-cyclohexyl rings which are unsubstituted or mono- or di-substituted by F and/or Cl atoms and/or CH₃ groups and/or CN groups, 4,4-disubstituted biphenyl, phenylcyclohexane and cyclohexylcyclohexane systems, 2,5-disubstituted pyrimidine and 1,3-dioxane rings 2,6-disubstituted naphthalene, dihydro- and tetrahydro-naphthalene, quinazoline and tetrahydroquinazoline,

| G is | —CH=CH— | —N(O)=N— |
|------|---------|----------|
|      | —CH=CY— | —CH=N(O)— |
|      | —C≡C—   | —CH₂—CH₂— |
|      | —CO—O—  | —CH₂—O—  |
|      | —CO—S—  | —CH₂—S—  |
|      | —CH=N—  | —COO—Phe—COO— | or a C—C single bond, Y is halogen, preferably chlorine or —CN, and R' and R" are alkyl, alkoxy, alkanoyloxy or alkoxycarbonyloxy having up to 18, preferably up to 8, carbon atoms, or one of these radicals can also be CN, NC, NO₂, CF₃, F, Cl or Br.

In most of these compounds, R' and R" are different, one of these radicals being an alkyl or alkoxy group in most cases. However, other variants of the substituents envisaged are also usual. Many such substances, or even mixtures of these, are commercially available. All these substances can be prepared by method's known from the literature.

The dielectrics according to the invention contain as a rule at least 30, preferably 50-99 and in particular 60-98 percent by weight of the compounds of the formula I and II. Preferably at least 5 percent by weight and in most cases even 10-40 percent by weight of these are represented one or more compounds of the formula I. However, the invention also comprises those liquid-crystalline dielectrics in which one or more compounds of the formula I amount only to less than 5 percent by weight, for example 0.1 to 3 percent by weight, for example for doping purposes, or amount to up to 60 percent by weight of the dielectrics according to the invention. Preferably, the liquid-crystalline dielectrics according to the invention contain 10 to 30 percent by weight of one or more compounds of the formula I.

The preparation of the dielectrics according to the invention is carried out in a manner conventional per se. As a rule, the components are dissolved in one another, preferably at an elevated temperature. By means of suitable additives, the liquid-crystalline dielectrics according to the invention can be modified such that they can be used in all hitherto disclosed types of liquid crystal display elements.

Such additives are known to those skilled in the art and are extensively described in the literature. By way of example, conductivity salts, preferably ethyl-dimethyldodecyl-ammonium 4-hexyloxybenzoate, tetrabutylammonium tetraphenylboranate or complex salts of crown ethers (cf., for example, I. Haller et al., Mol. Crys volume 24, pages 249–258(1973)) can be added for improving the conductivity, dichroic dyes can be added for preparing colored guest/host systems, or substances can be added for altering the dielectric anisotropy, the viscosity and/or the orientation of the nematic phases. Substances of this type are described, for example, in German Offenlegungsschriften 2,209,127, 2,240,864, 2,321,632, 2,338,281, 2,450,088, 2,637,430, 2,853,728 and 2,902,177.

The examples which follow are intended to illustrate the invention without restricting it. Percentage data above and below represent percent by weight; all temperatures are given in degrees Celsius. "Usual work-up" means: water is added, the mixture is extracted with methylene chloride, the phases are separated, the organic phase is dried and evaporated, and the product is purified by crystallization and/or chromatography.

EXAMPLE 1

A mixture of 400 g of trans-4-[trans-4-(trans-4-n-propylcyclohexylethyl)-cyclohexylethyl]-cyclohexanecarboxylic acid (obtainable by alkaline hydrolysis of p-[trans-4-(trans-4-n-propylcyclohexylethyl)-cyclohexylethyl]-benzonitrile (European Published Application No. 0 129,177) with KOH in diethylene glycol at 150° C., esterification of the resulting acid by boiling in ethanol in the presence of concentrated sulfuric acid, catalytic hydrogenation of the ester over an Rh catalyst under 3 bar and hydrolysis of the hydrogenated ester) and 100 g of n-pentanol is boiled in the presence of catalytic quantities of toluenesulfonic acid under a water separator and worked up as usual. This gives a pentyl trans-4-[trans-4-(trans-4-n-propylcyclohexylethyl)-cyclohexylethyl]-cyclohexanecarboxylate.

The following are prepared analogously:
methyl trans-4-[trans-4-(trans-4-n-propylcyclohexylethyl)cyclohexylethyl]-cyclohexanecarboxylate
ethyl trans-4-[trans-4-(trans-4-n-propylcyclohexylethyl)cyclohexylethyl]-cyclohexanecarboxylate
propyl trans-4-[trans-4-(trans-4-n-propylcyclohexylethyl)cyclohexylethyl]-cyclohexanecarboxylate
butyl trans-4-[trans-4-(trans-4-n-propylcyclohexylethyl)cyclohexylethyl]-cyclohexanecarboxylate
hexyl trans-4-[trans-4-(trans-4-n-propylcyclohexylethyl)cyclohexylethyl]-cyclohexanecarboxylate.

EXAMPLE 2

A mixture of 42.5 g of the amide of trans-4-[trans-4-(trans-4-n-propylcyclohexylethyl)-cyclohexylethyl]-cyclohexanecarboxylic acid (example 1), which is obtainable by converting the acid to the acid chloride and subsequent reaction with aqueous NH3 solution, 25 g of thionyl chloride and 200 ml of methylene chloride is boiled under reflux for 12 hours with stirring. After removal of the volatile constituents in vacuo, the residue is worked up as usual. This gives trans-4-[trans-4-(trans-4-n-propylcyclohexylethyl)-cyclohexylethyl]-cyclohexanecrbonitrile.

The following are prepared analogously:
trans-4-[trans-4-(trans-4-ethylcyclohexylethyl)-cyclohexanecarbonitrile
trans-4-[trans-4-(trans-4-butylcyclohexylethyl)-cyclohexanecarbonitrile
trans-4-[trans-4-(trans-4-pentylcyclohexylethyl)-cyclohexanecarbonitrile
trans-4-[trans-4-(trans-4-hexylcyclohexylethyl)-cyclohexanecarbonitrile
trans-4-[trans-4-(trans-4-heptylcyclohexyethyl)-cyclohexanecarbonitrile.

EXAMPLE 3

39.7 g of the nitrile prepared according to example 2 are reacted with 17.7 g of propylmagnesium bromide in a mixture of ether and benzene by the method of P. Canonne et al., Tetrahedron Letters 21, 155 (1980). After hydrolysis with aqueous hydrochloric acid, this gives 1-butyryl-trans-4-[trans-4-(trans-4-n-propylcyclohexylethyl)-cyclohexylethyl]-cyclohexane.

The following are prepared analogously:
1-acetyl-trans-4-[trans-4-(trans-4-n-propylcyclohexylethyl)cyclohexylethyl]-cyclohexane
1-propionyl-trans-4-[trans-4-(trans-4-n-propylcyclohexylethyl)-cyclohexylethyl]-cyclohexane
1-valeryl-trans-4-[trans-4-(trans-4-n-proylcyclohexylethyl)-cyclohexylethyl]-cyclohexane
1-hexanoyl-trans-4-[trans-4-(trans-4-n-propylcyclohexylethyl)-cyclohexylethyl]-cyclohexane
1-heptanoyl-trans-4-[trans-4-(trans-4-n-propylcyclohexylethyl)-cyclohexylethyl]-cyclohexane

EXAMPLE 4

23.8 g of NaBH4 are added portion by portion to 38.6 g of the toluenesulfonylhydrazone of the ketone from example 3 in 1050 ml of glacial acetic acid, and the mixture is stirred overnight. The solvent is then removed in vacuo, and the residue is hydrolysed and worked up as usual. This gives 1-butyl-trans-4-[trans-(trans-4-n-propylcyclohexylethyl)-cyclohexylethyl]-cyclohexane.

The following are prepared analogously:
1-ethyl-trans-4-[trans-4-(trans-4-n-propylcyclohexylethyl)-cyclohexylethyl]-cyclohexane
1-propyl-trans-4-[trans-4-(trans-4-n-propylcyclohexylethyl)-cyclohexylethyl]-cyclohexane
1-butyl-trans-4-[trans-4-(trans-4-n-propylcyclohexylethyl)-cyclohexylethyl]-cyclohexane
1-hexyl-trans-4-[trans-4-(trans-4-n-propylcyclohexylethyl)-cyclohexylethyl]-cyclohexane
1-heptyl-trans-4-[trans-4-(trans-4-n-propylcyclohexylethyl)-cyclohexylethyl]-cyclohexane.

EXAMPLE 5

A solution of 41 g of the ketone obtainable from p[trans-4-(trans-4-n-propylcyclohexylethyl)-cyclohexylethyl]benzonitrile and propylmagnesium bromide in 500 ml of tetrahydrofuran is hydrogenated at room temperature and normal pressure over 30 g of Pd-on-C (5% as the catalyst. After the absorption of hydrogen has ceased, the filtrate is worked up as usual. This gives p-[trans-(trans-4-n-propylcyclohexylethyl)-cyclohexylethyl]-butylbenzene.

The following are prepared analogously:

p-[trans-4-(trans-4-propylcyclohexylethyl-cyclohexylethyl]-methylbenzene
p-[trans-4-(trans-4-propylcyclohexylethyl-cyclohexylethyl]-ethylbenzene
p-[trans-4-(trans-4-propylcyclohexylethyl-cyclohexylethyl]-propylbenzene
p-[trans-4-(trans-4-propylcyclohexylethyl)-cyclohexylethyl]-pentylbenzene
p-[trans-4-(trans-4-propylcyclohexylethyl)-cyclohexylethyl]-heptylbenzene
p-[trans-4-(trans-4-butylcyclohexylethyl)-cyclohexylethyl]-methylbenzene p-[trans-4-(trans-4-butylcyclohexylethyl)-cyclohexylethyl]-ethylbenzene
p-[trans-4-(trans-4-butylcyclohexylethyl)-cyclohexylethyl]-propylbenzene
p-[trans-4-(trans-4-butylcyclohexylethyl)-cyclohexylethyl]-butylbenzene
p-[trans-4-(trans-4-butylcyclohexylethyl)-cyclohexylethyl]-pentylbenzene
p-[trans-4-(trans-4-butylcyclohexylethyl-cyclohexylethyl]-heptylbenzene p-[trans-4-(trans-4-pentylcyclohexylethyl)-cyclohexylethyl]-methylbenzene
p-[trans-4-(trans-4-pentylcyclohexylethyl)-cyclohexylethyl]-ethylbenzene
p-[trans-4-(trans-4-pentylcyclohexylethyl)-cyclohexylethyl]-propylbenzene
p-[trans-4-(trans-4-pentylcyclohexylethyl)-cyclohexylethyl]-butylbenzene
p-[trans-4-(trans-4-pentylcyclohexylethyl)-cyclohexylethyl]-pentylbenzene
p-[trans-4-(trans-4-pentylcyclohexylethyl)-cyclohexylethyl]-heptylbenzene

EXAMPLE 6

A few milliliters of a solution of 50 g of p-bromoanisole in 50 ml of THF are added dropwise under a nitrogen atmosphere and with the exclusion of moisture to 6.5 g of magnesium filings and 30 ml of tetrahydrofuran (THF), until the Grignard reaction has started. The remainder of the bromoanisole solution is then diluted with 150 ml of THF and added dropwise to the boiling reaction mixture. The reaction mixture is boiled for 1 hour under reflux, and a solution of 73.4 g of trans-4-(trans-4-n-propylcyclohexylethyl)-cyclohexylacetonitrile (obtainable from trans-4-(trans-4-n-propylcyclohexylethyl)-cyclohexanecarboxylic acid by reduction with LiAlH$_4$, conversion of the resulting alcohol to the corresponding mesylate and nucleophilic substitution of the mesylate radical for nitrile) in 200 ml of toluene is then added. THF is distilled off from the reaction mixture until a reaction temperature of 110° C. has been reached. At this temperature, the reaction mixture is stirred for 2 hours. After cooling to room temperature, 500 ml of water are added and the mixture is acidified with concentrated HCl. 300 ml of THF and 300 ml of methyl tertiary-butyl ether are then added, the aqueous phase is separated off and the organic phase is washed several times with water and then dried and evaporated The residue is recrystallized from ethanol, taken up in 750 ml of THF and hydrogenated at room temperature at normal pressure with 40 g of Pd/C (5%). After the catalyst has been filtered off, the solution is evaporated and the residue is purified by chromatography and crystallization. This gives p-[trans-4-(trans-4-propylcyclohexylethyl)-cyclohexlethyl]-methoxybenzene.

The same product is obtained when trans-4-(trans-4-n-propylcyclohexylethyl)-cyclohexylacety chloride in toluene is reacted with anisole in the presence of SnCl$_4$ as a catalyst and hydrogenated as described The following are prepared analogously:
p-[trans-4-(trans-4-propylcyclohexylethyl)-cyclohexylethyl]-ethoxybenzene
p-[trans-4-(trans-4-propylcyclohexylethyl)-cyclohexylethyl]-propoxybenzene
p-[trans-4-(trans-4-propylcyclohexylethyl)-cyclohexylethyl]-butoxybenzene
p-[trans-4-(trans-4-propylcyclohexylethyl)-cyclohexylethyl]-pentoxybenzene p-[trans-4-(trans-4-pentylcyclohexylethyl)-cyclohexylethyl]-methoxybenzene
p-[trans-4-(trans-4-entylcyclohexylethyl)-cyclohexylethyl]-ethoxybenzene
p-[trans-4-(trans-4-pentylcyclohexylethyl-cyclohexylethyl]-propoxybenzene
p-[trans-4-(trans-4-pentylcyclohexylethyl-cyclohexylethyl]-butoxybenzene
p-[trans-4-(trans-4-pentylcyclohexylethyl)-cyclohexylethyl]-pentoxybenzene

EXAMPLE 7

A mixture of 40 g of p-[trans-4 -n-propylcyclohexylethyl)-cyclohexylethyl]- ethoxybenzene and 40 g of potassium tert -butylate in 300 ml of N-methylpyrrolidone (NMP) is stirred for 20 hours at 160° C. under a nitrogen atmosphere, the volatile components being distilled off. After the mixture has been cooled to about 90° C., it is carefully added to a mixture of 500 g of ice and 100 ml of concentrated HCl. The product thus precipitating is washed with water and recrystallized from ethyl acetate. This gives p-[trans-4-(trans-4-propylcyclohexylethyl)cyclohexylethyl)-phenol.

The following are prepared analogously:
p-[trans-4-(trans-4-methylcyclohexylethyl)-cyclohexylethyl]-phenol
p-[trans-4-(trans-4-ethylcyclohexylethyl)-cyclohexylethyl]-phenol
p-[trans-4-(trans-4-butylcyclohexylethyl)-cyclohexylethyl]-phenol
p-[trans-4-(trans-4-pentylcyclohexylethyl)-cyclohexylethyl]-phenol
p-[trans-4-(trans-4-heptylcyclohexylethyl)-cyclohexylethyl]-phenol.

EXAMPLE 8

A mixture of 3.5 g of potassium carbonate, 8.1 g of p-[trans-4-(trans-4-n-propylcyclohexylethyl)-cyclohexylethyl]-phenol, 4.95 g of optically active 2-methylbutyl iodide and 50 ml of DMF is stirred for 12 hours at 110° C. The mixture is then worked up as usual, and the product is purified by chromatography and crystallization.

This gives-optically active p-[trans-4-(trans-4-n-propylcyclohexylethyl)-cyclohexylethyl]-[2-methylbutoxy]benzene.

EXAMPLE 9

36.8 g of butyric acid chloride are added to a mixture of 122.8 g of p-[trans-4-(trans-1-n-propylcyclohexylethyl)-cyclohexylethyl]-phenol, 28 ml of pyridine and 1.5 l of toluene. Subsequently, the reaction mixture is stirred for 3 hours at 70° C. and then worked up as usual, and the product is purified by chromatography and crystallization. This gives p-[trans-4-(trans-4-propylcyclohexylethyl)-cyclohexylethyl]-butyryloxybenzene.

EXAMPLE 10

With exclusion of atmospheric oxygen and moisture, a solution of 30.3 g of trans-4-(trans-4-n-pentylcyclohexylethyl)-cyclohexylacetonitrile in 100 ml of toluene is added at the boil to a Grignard reagent prepared from 17.5 g of p-bromofluorobenzene and 2.5 g of magnesium filings in 40 ml of THF. THF is distilled off from the reaction mixture until a reaction temperature of 110° C. has been reached After a reaction period of 2 hours, the batch is allowed to cool and is worked up as usual.

The reaction product is taken up in 300 ml of THF and hydrogenated with 40 g of Pd/C (5%) at room temperature and normal pressure. This gives p-[trans-4-pentylcyclohexylethyl)-cyclohexylethyl]-fluorobenzene.

The following are prepared analogously:
p-[trans-4-(trans-4-ethylcyclohexylethyl)-cyclohexylethyl]-fluorobenzene
p-[trans-4-(trans-4-propylcyclohexylethyl)-cyclohexylethyl]-fluorobenzene
p-[trans-4-(trans-4-butylcyclohexylethyl)-cyclohexylethyl]-fluorobenzene
p-[trans-4-(trans-4-hexylcyclohexylethyl)-cyclohexylethyl]-fluorobenzene
p-[trans-4-(trans-4-heptylcyclohexylethyl)-cyclohexylethyl]-fluorobenzene With the Grignard reagent prepared from 3,4-difluorobromobenzene, the following are obtained analogously:
4-[trans-4-(trans-4-ethylcyclohexylethyl)-cyclohexylethyl]-1,2-difluorobenzene
4-[trans-4-(trans-4-propylcyclohexylethyl)-cyclohexylethyl]-1,2-difluorobenzene
4-[trans-4-(trans-4-butylcyclohexylethyl)-cyclohexylethyl]-1,2-difluorobenzene
4-[trans-4-(trans-4-pentylcyclohexylethyl)-cyclohexylethyl]-1,2-difluorobenzene
4-[trans-4-(trans-4-hexylcyclohexylethyl)-cyclohexylethyl]-1,2-difluorobenzene
4-[trans-4-(trans-4-heptylcyclohexylethyl)-cyclohexylethyl]-1,2-difluorobenzene.

EXAMPLE 11

The ketone obtained by reacting. The Grignard reagent prepared from 65 g of p-trans-4-propylcyclohexyl-bromobenzene and 6.7 g of magnesium filings with 75.8 g of trans-4-(trans-4-n-pentylcyclohexylethyl-cyclohexylacetonitrile is dissolved in 500 ml of methyl tert.-butyl ether and reacted with 42 ml of a 70% solution of sodium bis-(2-methoxymethoxy)-aluminum dihydride at the boil, while excluding atmospheric oxygen and moisture The mixture is worked up as usual and the product is then heated in 1.5 l of toluene in the presence of 5 g of p-toluenesulfonic acid under a water separator. The mixture is then worked up as usual, and the product is taken up in 100 ml of THF and hydrogenated over 30 g of Pd/C (5%) at room temperature and normal pressure. The product is purified by chromatography. This gives 4-[trans-4-(trans-4-pentylcyclohexylethyl)cyclohexylethyl]-1-(trans-4-propylcyclohexyl)-benzene.

The following are prepared analogously:
4-[trans-4-(trans-4-pentylcyclohexylethyl)-cyclohexylethyl]-1-(trans-4-ethylcyclohexyl)-benzene
4-[trans-4-(trans-4-pentylcyclohexylethyl)-cyclohexylethyl]-1-(trans-4-butylcyclohexyl)-benzene
4-[trans-4-(trans-4-pentylcyclohexylethyl)-cyclohexylethyl]-1-(trans-4-pentylcyclohexyl)-benzene
4-[trans-4-(trans-4-butylcyclohexylethyl)-cyclohexylethyl]-1-(trans-4-ethylcyclohexyl)-benzene
4-[trans-4-(trans-4-butylcyclohexylethyl)-cyclohexylethyl]-1-(trans-4-propylcyclohexyl)-benzene
4-[trans-4-(trans-4-butylcyclohexylethyl)-cyclohexylethyl]-1-(trans-4-butylcyclohexyl)-benzene
4-[trans-4-(trans-4-butylcyclohexylethyl)-cyclohexylethyl]-1-(trans-4-pentylcyclohexyl)-benzene 4-[trans-4-(trans-4-propylcyclohexylethyl)-cyclohexylethyl]-1-(trans-4-ethylcyclohexyl)-benzene
4-[trans-4-(trans-4-propylcyclohexylethyl)-cyclohexylethyl]-1-(trans-4-propylcyclohexyl)-benzene
4-[trans-4-(trans-4-propylcyclohexylethyl)-cyclohexylethyl]-1-(trans-4-butylcyclohexyl)-benzene
4-[trans-4-(trans-4-propylcyclohexylethyl)-cyclohexylethyl]-1-(trans-4-pentylcyclohexyl)-benzene 4-[trans-4-(trans-4-ethylcyclohexylethyl)-cyclohexylethyl]-1-(trans-4-ethylcyclohexyl)-benzene
4-[trans-4-(trans-4-ethylcyclohexylethyl-cyclohexylethyl]-1-(trans-4-propylcyclohexyl)-benzene
4-[trans-4-(trans-4-ethylcyclohexylethyl-cyclohexylethyl]-1-(trans-4-butylcyclohexyl)-benzene
4-[trans-4-(trans-4-ethylcyclohexylethyl)-cyclohexylethyl]-1-(trans-4-pentylcyclohexyl)-benzene.

EXAMPLE 12

A hypobromite solution prepared from 2 g of sodium hydroxide and 1.6 g of bromine in 25 ml of ice-water is added to a suspension of 0.87 g of 4-[trans-4-(trans-4-pentylcyclohexylethyl)-cyclohexylethyl]-2-fluoroacetophenone in 50 ml of dioxane. The mixture is stirred for 12 hours at 40° C. and then acidified with concentrated hydrochloric acid. The acid which has precipitated is recrystallized from glacial acetic acid and boiled for 3 hours under reflux with 5 g of thionyl chloride. The excess thionyl chloride is stripped off in vacuo and the residue is taken up in acetone and added to 20 ml of an aqueous NH$_3$ solution. The acid amide is washed thoroughly with water, dried in vacuo at 80° C. and boiled, with stirring, with 10 ml of thionyl chloride in the presence of a catalytic quantity of DMF. The mixture is then worked up as usual. This gives 4-[trans-4-(trans-4-pentylcyclohexylethyl)-cyclohexylethyl]-2-fluorobenzonitrile.

The following are prepared anomalously:
4-[trans-4-(trans-4-heptylcyclohexylethyl)-cyclohexylethyl]-2-fluorobenzonitrile
4-[trans-4-(trans-4-butylcyclohexylethyl)-cyclohexylethyl]-2-fluorobenzonitrile
4-[trans-4-(trans-4-propylcyclohexylethyl)-cyclohexylethyl]-2-fluorobenzonitrile
4-[trans-4-(trans-4-ethylcyclohexylethyl-cyclohexylethyl]-2-fluorobenzonitrile.

EXAMPLE 13

9.65 g of 3,4-difluorobromobenzene in 10 ml of THF are added to 1.23 g of magnesium in 30 m of THF, while excluding atmospheric oxygen and moisture. The reaction mixture is boiled under reflux until the magnesium filings have completely dissolved. The Grignard solution is cooled to room temperature and added to a solution of 3.4 g of ZnCl$_2$ in 25 ml of THF, while cooling with ice. After 30 minutes, 0.33 g of dichloro-bis-triphenylphosphine-nickel (II) and then a solution of 21 g of p-[trans-4-(trans-4-n-propylcyclohexylethyl)-cyclohexylethyl]-bromobenzene in 40 ml of THF are added. The mixture is stirred for 48 hours at room temperature and then worked up as usual. The product is purified by chromatography and crystallization. This gives 4-[trans-4-(trans-4-n-propylcyclohexylethyl)-cyclohexylethyl]-3,4-difluorobiphenyl.

The following are prepared analogously:
4-[trans-4-(trans-4-ethylcyclohexylethyl)-cyclohexylethyl]-3,4-difluorobiphenyl
4-[trans-4-(trans-4-butylcyclohexylethyl)-cyclohexylethyl]-3,4-difluorobiphenyl
4-[trans-4-(trans-4-pentylcyclohexylethyl)-cyclohexylethyl]-3,4-difluorobiphenyl
4-[trans-4-(trans-4-heptylcyclohexylethyl)-cyclohexylethyl]-3,4-difluorobiphenyl The following are examples of liquid-crystalline phases according to the invention:

EXAMPLE A

A liquid crystal phase consisting of
6% of 2-p-cyanophenyl-5-propyl-1,3-dioxane,
6% of 2-p-cyanophenyl-5-butyl-1,3-dioxane,
10% of p-trans-4-propylcyclohexylbenzonitrile,
6% of trans,trans-4'-ethoxycyclohexyl-4-propylcyclohexane,
8% of trans,trans-4'-methoxycyclohexyl-4-pentylcyclohexane,
12% of trans,trans-4'-ethoxycyclohexyl-4-propylcyclohexane,
12% of trans,trans-4'-butyryloxycyclohexyl-4-propylcyclohexane,
3% of trans-4-propylcyclohexyl trans,trans-4-propylcyclohexylcyclohexane-4-carboxylate,
3% of trans-4-pentylcyclohexyl trans,trans-4-propylcyclohexylcyclohexane-4-carboxylate,
3% of trans-4-propylcyclohexyl trans,trans-4-butylcyclohexylcyclohexane-4-carboxylate,
3% of trans-4-pentylcyclohexyl trans,trans-4-butylcyclohexylcyclohexane-4-carboxylate,
3% of 1-propyl-trans-4-[trans-4-(trans-propylcyclohexylethyl)-cyclohexylethyl]-cyclohexane,
3% of 1-pentyl-trans-4-[trans-4-(trans-propylcyclohexylethyl)-cyclohexylethyl]-cyclohexane,
3% of 4,4'-bis-(trans-4-propylcyclohexyl)-2-fluorobiphenyl,
4% of 4,4'-bis-(trans-4-pentylcyclohexyl)-2-fluorobiphenyl and
4% of 4-(trans-4-pentylcyclohexyl)-4'-(trans-4-propylcyclohexyl)-2-flourobiphenyl
has no smectic/nematic phase transition down to −40°, a viscosity of 19×10$^{-3}$ (780×10$^{-3}$) Pa. at 20° (−30°), an optical anisotropy of 0.084 and a threshold voltage of 2.7 volt. This phase is distinguished by a positive dielectric anisotropy, a high clear point and a wide nematic range.

EXAMPLE B

A liquid crystal phase consisting of
16% of p-trans-4-propylcyclohexylbenzonitrile,
9% of p-trans-4-butylcyclohexylbenzonitrile,
12% of trans,trans-4'-propoxycyclohexyl-4-propylcyclohexane,
12% of trans,trans-4'-methoxycyclohexyl-4-pentylcyclohexane,
12% of trans,trans-4'-ethoxycyclohexyl-4-propylcyclohexane,
12% of trans,trans-4'-propylcyclohexyl-4-propylcyclohexane,
12% of 1-pentyl-trans-4-[trans-4-(trans-4-propylcyclohexylethyl)-cyclohexylethyl]-cyclohexane,
3% of 4,4'-bis-(trans-4-propylcyclohexyl)-2-fluorobiphenyl,
2% of 4,4'-bis-(trans-4-pentylcyclohexyl)-2-fluorobiphenyl,
5% of 4-(trans-4-pentylcyclohexyl)-4'-(trans-4-propylcyclohexyl)-2-fluorobiphenyl
3% of 4,4'-bis-(trans-4-propylcyclohexyl)-biphenyl and
3$ of 4-(trans-4-pentylcyclohexyl)-4'-(trans-4-propylcyclohexyl)-biphenyl
has an optical anisotropy of 0.084 and threshold voltage of 2.5 volt.

We claim:

1. A cyclohexane derivative of the formula I

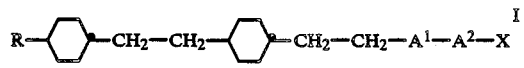

in which
R is an alkyl group which has 1–12 C atoms and in which one or two non-adjacent CH$_2$ groups can also be replaced by O, —CO—O— or —OCO—,
A$^1$ and A$^2$ each independently of one another are trans-1,4cyclohexylene or unsubstituted or fluorine-substituted 1,4-phenylene, and one of the groups A$^1$ and A$^2$ can also be a single bond,
X is fluorine or chlorine.

2. A liquid-crystalline phase having at least two liquid-crystalline components, wherein at least one component is a compound of claim 1.

3. A liquid crystal display element containing a liquid-crystalline phase, wherein the phase is one of claim 2.

4. An electro-optical display element containing a liquid-crystalline dielectric, wherein the dielectric is a phase of claim 2.

5. A cyclohexane derivative of claim 1, wherein R is a straight-chain alkyl group with 2 to 10 carbon atoms.

6. A cyclohexane derivative of claim 1, wherein A$^1$–A$^2$ is Phe, PhF, Phe-Phe, PhF-Phe or Phe-PhF, Phe is a 1,4-phenylene group and PhF is a fluorine-substituted 1,4-phenylene group.

7. A cyclohexane derivative of claim 6, wherein A$^1$–A$^2$ is PHF or Phe-PhF and the fluorine atom in PhF is in the ortho-position to X.

8. A cyclohexane derivative of claim 7, wherein X is fluorine.

9. A cyclohexane derivative of claim 6, wherein A$^1$–A$^2$ is Phe.

10. A cyclohexane derivative of claim 9, wherein X is fluorine.

* * * * *